United States Patent [19]
Wilk et al.

[11] Patent Number: 5,482,041
[45] Date of Patent: Jan. 9, 1996

[54] MEDICAL INVESTIGATION SYSTEM AND RELATED METHOD

[76] Inventors: Peter J. Wilk, 185 West End Ave., New York, N.Y. 10023; Robert C. Stirbl, 247 Wadsworth Ave., New York, N.Y. 10033

[21] Appl. No.: 232,674

[22] Filed: Apr. 25, 1994

Related U.S. Application Data

[63] Continuation-in-part of Ser. No. 894,081, Jun. 5, 1992, Pat. No. 5,305,748.

[51] Int. Cl.$^6$ ........................................... A61B 6/00
[52] U.S. Cl. ................................ 128/653.1; 128/665
[58] Field of Search ........................ 128/653.1, 653.2, 128/664, 665, 633, 634

[56] References Cited

U.S. PATENT DOCUMENTS

| | | | |
|---|---|---|---|
| 4,556,057 | 12/1985 | Hiruma et al. | |
| 4,569,354 | 2/1986 | Shapiro et al. | 128/665 |
| 5,131,398 | 7/1992 | Alfano et al. | 128/665 |
| 5,253,646 | 10/1993 | Delpy et al. | 128/665 |
| 5,363,050 | 11/1994 | Guo et al. | 324/638 |
| 5,369,496 | 11/1994 | Alfano et al. | 128/665 |

OTHER PUBLICATIONS

J. J. Lee, "Lens Antennas" in *Antenna Handbook: Theory, Applications and Design*. (Van Nostrand Reinhold Co., New York). 1988.

*Primary Examiner*—Ruth S. Smith
*Attorney, Agent, or Firm*—R. Neil Sudol; Henry D. Coleman

[57] ABSTRACT

In a medical diagnostic method a patient is supported in a predetermined position and microwave energy is focused on a predetermined target region in the patient to produce a burst of photoluminescence. Electromagnetic radiation emitted from organic cellular material at the focal point or the microwave radiation is automatically detected. In a subsequent step, a spectral output of the organic cellular material is automatically determined from electromagnetic radiation received from the radiation focal point through the patient during the step of detecting. In addition, a diagnosis of the excited cellular material is automatically implemented based on the results of the spectral analysis.

42 Claims, 3 Drawing Sheets

MEDICAL INVESTIGATION SYSTEM AND RELATED METHOD

CROSS-REFERENCE TO RELATED APPLICATION

This application is a continuation-in-part of U.S. Pat. application Ser. No. 07/894,081 filed Jun. 5, 1992, now U.S. Pat. No. 5,305,748.

BACKGROUND OF THE INVENTION

This invention relates to a system and an associated method for use in obtaining medical type information. Such information is useful eventually in making diagnoses and implementing treatments. More particularly, this invention relates to a non-invasive medical examination technique for determining molecular composition of tissue samples internal to a patient.

Substantial advances have been made in the last twenty years in ascertaining internal organic structures without surgery. CAT scanners and nuclear magnetic resonance (NMR) imaging devices, as well as ultrasonography, have provided the physician with powerful tools for use in diagnosing patients. However, although these tools provide images of internal organic structures such as tumorous growths, those tools cannot provide any information as to whether a growth is malignant or benign. Generally, to make a definitive diagnosis as to potential malignancy of cancerous growths in the internal tissues of a patient, an incision must be made and a sample of the suspect tissues removed in a biopsy procedure. Such an invasive procedure is time consuming, expensive and traumatic to the patient.

OBJECTS OF THE INVENTION

An object of the present invention is to provide a new system and a related new technique for obtaining medical or diagnostic type information as to internal tissues of a patient.

Another object of the present invention is to provide such a system and method which provides medical or diagnostic type information as to internal tissues which is relatively non-invasive.

A further object of the present invention is to provide such a system and method which provides medical or diagnostic type information as to internal tissues without the performance of a biopsy.

A further object of the present invention is to provide such a system and device which is automated.

Other objects of the present invention will be apparent from the detailed descriptions and drawings included herein.

SUMMARY OF THE INVENTION

A medical tissue investigation method comprises, in accordance with the present invention, the steps of (a) generating electromagnetic energy having a predetermined first frequency, (b) transmitting the first frequency along a predetermined first line extending through a patient, (c) also generating electromagnetic energy having a predetermined second frequency different from the first frequency, and (d) transmitting the second frequency along a predetermined second line extending through the patient at a predetermined angle relative to the first line, the second line intersecting the first line at one predetermined point inside the patient, the steps of transmitting being performed simultaneously. The method also comprises the steps of (e) automatically detecting electromagnetic radiation emitted from organic cellular material at the predetermined point in response to excitation of the cellular material by the first frequency and the second frequency upon simultaneous irradiation of the predetermined point by the first frequency and the second frequency, and (f) automatically determining a spectral output of the organic cellular material from electromagnetic radiation received from the predetermined point through the patient during the step of detecting.

In a procedure in accordance with the present invention, electromagnetic radiation of the first frequency and electromagnetic radiation of the second frequency are concentrated at a series of points within the patient. The points may be disposed along a line extending through the patient. Generally, where a patient points to a region of localized pain, the tissues of the patient are tested along a line extending generally perpendicularly to the patient's skin surface at the point indicated by the patient. That test line may be the first line, along which radiation of the first frequency is transmitted, or the second line, along which radiation of the second frequency is transmitted. In the former case, the first frequency is transmitted along the first line during the testing procedure, while the second frequency is transmitted along a series of second lines, each such second line being oriented at a different angle relative to the first line, thereby enabling irradiation of a series of different points with energy of the first frequency and the second frequency. Alternatively, both the first line and the second line may change, to define a third line along which the test points are located.

The principle underlying the above described methodology is that the spectral output of a particular organic molecule, and or atoms included in that molecule, will change depending on the multiple excitation frequencies used. Thus, molecules or a certain kind located at points irradiated by only one of the two frequencies will have a different spectral output than those molecules of the same kind located at the commonly irradiated (predetermined) point. This difference enables a differentiation of tissue responses in accordance with tissue locations.

According to another feature of the present invention, electromagnetic energy having a predetermined third frequency is generated and transmitted along a predetermined third line extending through the patient at a predetermined angle relative to the first line (the line of transmission of the first frequency). The third line intersects the first line at the predetermined point inside the patient. The line of transmission of the third frequency may be the same as or different from the line of transmission of the second frequency. The third frequency impinges upon the predetermined point at the same time as the first frequency. Electromagnetic radiation emitted from the organic cellular material at the predetermined point in response to excitation of the cellular material by the first frequency and the third frequency is automatically detected upon simultaneous irradiation of the predetermined point by the first frequency and the third frequency. A spectral output of the organic cellular material from electromagnetic radiation received from the predetermined point through the patient is automatically determined.

According to this feature of the present invention, one or more test points in the patient are subjected to different combinations of frequencies. Thus, different types of molecules at the test point(s) may be ascertained.

In order to investigate a series of test points within the patient, the second frequency is directed along an additional line extending through the patient at another predetermined angle relative to the first line, the additional line intersecting the first line at an additional predetermined point inside the patient. The directing step is performed simultaneously with the step of transmitting the first frequency. Again, electromagnetic radiation emitted from the organic cellular material at the additional predetermined point in response to excitation of the cellular material by the first frequency and the second frequency is automatically detected upon simultaneous irradiation of the additional predetermined point by the first frequency and the second frequency. Again, the spectral output of the organic cellular material from electromagnetic radiation received from the predetermined point through the patient is automatically determined.

According to an additional feature of the present invention, electrical signals are produced encoding a first angle identifying the first line and a second angle identifying the second line, and, in response to the electrical signals, a location of the predetermined point relative to the patient is computed.

According to a specific feature of the present invention, the first frequency is transmitted in the form of a narrow beam (e.g., collimated radiation or laser generated radiation) along the first line into or through the patient. The second frequency is then concentrated at a controlled or predetermined series of points along the first line. To achieve that end, the second frequency is transmitted in the form of a narrow beam (e.g., collimated radiation or laser generated radiation) along the second line into or through the patient.

The narrow beams of the first and the second frequency may be produced by operating respective lasers. Alternatively or additionally, the narrow beams may be produced by collimating the first frequency and collimating the second frequency.

It is to be noted that the first frequency and/or the second frequency may be concentrated at the predetermined test or target point by respectively focusing the first frequency and/or focusing the second frequency at the predetermined point. In this case, the irradiating energy is not collimated but rather transmitted in a beam which converges to the predetermined test or target point.

According to a further feature of the present invention, the first frequency and the second frequency are emitted from a hand-held transceiver device. Photodetectors may be disposed on the transceiver device for picking up the electromagnetic output of the stimulated test or target region. Where the irradiating energy is produced in the form of laser energy, the laser energy may be guided along fiber optic cables to the hand-held device from one or more laser sources.

According to another feature of the present invention, characteristics or parameters of an irradiating waveform other than frequency or wavelength may be varied, to obtain further information as to the nature of the tissues at a predetermined test point. For example, the phase, the amplitude and/or the polarization of the second frequency may be varied during successive stages of an investigative procedure in accordance with the present invention. The second frequency with the modified phase, amplitude, and/or polarization may be transmitted along the second line through the patient simultaneously with a continued or repeated transmission of the first frequency along the first line. The detection and spectral determination steps are repeated with each change in a characteristic or parameter of the second irradiating frequencies.

More generally stated, a medical tissue investigation method comprises, in accordance with the present invention, the steps of (1) generating electromagnetic energy characterized by a preselected wavelength, a preselected amplitude, and a preselected polarization, (2) concentrating the energy towards a predetermined point internal to the patient, (3) transmitting the energy through the patient to the predetermined point, (4) automatically detecting electromagnetic radiation emitted from organic cellular material at the predetermined point in response to excitation of the cellular material by the energy upon concentration thereof at the predetermined point, and (5) automatically determining, from electromagnetic radiation received from the predetermined point through the patient during the step of detecting, a radiation output of the organic cellular material characterized by wavelength, amplitude, and polarization.

At least one of the preselected wavelength, the preselected amplitude, and the preselected polarization may be varied automatically in accordance with a preprogrammed sequence. The location of the predetermined point may also be changed, i.e., a plurality of predetermined test or target points may be irradiated. Each such test or target point may be successively subjected to radiation of different frequencies, different phases, different amplitudes, and/or different polarizations.

To further facilitate discrimination among the spectral responses of organic tissues at different locations within the patient, at least one of the first frequency and the second frequency may be modulated prior to the transmission thereof into or through the patient. The modulation may be implemented by operating a phase locked modulator. During the detection process, an electrical signal is generated by operating a phase locked amplifier.

Accordingly, a medical tissue investigation method comprises, in accordance with the present invention, the steps of (i) generating electromagnetic energy having a predetermined plurality of wavelengths, (ii) modulating at least one of the wavelengths, (iii) transmitting the energy including the modulated wavelength through the patient to the predetermined point, and (iv) automatically detecting electromagnetic radiation emitted from organic cellular material at the predetermined point in response to excitation of the cellular material by the energy including the modulated wavelength upon transmission thereof to the predetermined point, the step of detecting including the step of filtering out extraneous background noise in incoming electromagnetic radiation having the one of the wavelengths. In another step (v), a spectral output of the organic cellular material is automatically determined from electromagnetic radiation received from the predetermined point through the patient during the step of detecting.

A medical tissue investigation method comprises, in accordance with another feature of the present invention, the steps of (A) generating electromagnetic energy having a predetermined plurality of wavelengths, (B) transmitting the energy through the patient to a predetermined point internal to the patient, (C) concentrating the energy at the predetermined point, (D) automatically determining the location of the predetermined point relative to the patient, (E) automatically detecting electromagnetic radiation emitted from organic cellular material at the predetermined point in response to excitation of the cellular material by the energy upon focusing thereof on the predetermined point, (F) automatically determining a spectral output of the organic cellular material from electromagnetic radiation received from the predetermined point through the patient during the step of detecting, and (G) correlating the determined spectral output of the organic cellular material with the location of the predetermined point relative to the patient.

According to a more particular feature of the present invention, determining the location of the predetermined point includes the step of operating a wireless imaging device such as a CAT scanner or an MRI apparatus.

Alternatively or additionally, the location of the predetermined point may be determined by automatically monitoring a direction of transmission of the energy through the patient. If the directions of transmission of two beams of energy energy through the patient are determined, then the location of the point of intersection can be calculated. This trigonometric calculation can be used whether the irradiating energy is transmitted in collimated beams or converging beams.

A medical tissue investigation system comprises, in accordance with the present invention, a first generator for generating electromagnetic energy having a predetermined first frequency, a first directional transmitter for transmitting the first frequency along a predetermined first line extending through a patient, a second generator for generating electromagnetic energy having a predetermined second frequency different from the first frequency, and a second directional transmitter for transmitting the second frequency along a predetermined second line extending through the patient at a predetermined angle relative to the first line, the second line intersecting the first line at one predetermined point inside the patient. A photoelectric detector or detector array is provided for automatically detecting electromagnetic radiation emitted from organic cellular material at the predetermined point in response to excitation of the cellular material by the first frequency and the second frequency upon simultaneous irradiation of the predetermined point by the first frequency and the second frequency. A computer is operatively connected to the detector for automatically determining a spectral output of the organic cellular material from electromagnetic radiation received from the predetermined point through the patient.

Pursuant to another feature of the present invention, the computer is operatively connected to at least one of the first generator and the second generator for controlling that generator to change a respective one of the first frequency and the second frequency. Thus, the computer can change the frequency in accordance with a preprogrammed sequence. The order of such a sequence is generally unimportant. However, the order is predetermined in order to facilitate correlation of the measured spectral output with the irradiating frequencies.

Pursuant to another feature of the present invention, the computer is operatively connected to at least one of the directional transmitters for controlling that transmitter to change a respective line or direction of transmission. In that case, the respective directional transmitter is provided with means responsive to signals from the computer for changing the angle or direction of radiation transmission.

Pursuant to a further feature of the present invention, the second generator includes means for changing at least one of an amplitude, a phase and a polarization of the second frequency.

Pursuant to another feature of the present invention, at least one of the first generator and the second generator includes a laser for generating a respective one of the first frequency and the second frequency. Alternatively or additionally, at least one of the generators includes means for collimating a respective one of the first frequency and the second frequency.

Pursuant to yet another feature of the present invention, a signal generator is operatively connected to the transmitters for producing electrical signals encoding a first angle identifying the first line and a second angle identifying the second line. The computer is then operatively connected to the signal generator for computing a location of the predetermined point relative to the patient in response to the electrical signals.

Pursuant to an additional feature of the present invention, a modulator is provided and is included in or connected to one of the generators for modulating at least one of the first frequency and the second frequency prior to the transmission thereof through the patient. The modulator may take the form of a phase locked modulator, whereas the detector includes a phase locked amplifier for generating an electrical signal encoding incoming detected electromagnetic energy.

Pursuant to yet a further feature of the present invention, the system also comprises a portable transceiver device. The transmitters are disposed on the transceiver device, and the detector includes a photoelectric transducer which is also disposed on the transceiver device.

A medical tissue investigation system comprises, in accordance with another conceptualization of the present invention, (I) a generator for generating electromagnetic energy characterized by a preselected wavelength, a preselected amplitude, and a preselected polarization, (II) a transmitter for transmitting the energy through the patient to the predetermined point, (III) a detector for automatically detecting electromagnetic radiation emitted from organic cellular material at the predetermined point in response to excitation of the cellular material by the energy upon concentration thereof at the predetermined point, and (IV) a computer operatively connected to the detector for automatically determining, from electromagnetic radiation received from the predetermined point through the patient during the step of detecting, a radiation output of the organic cellular material characterized by wavelength, amplitude, and polarization. The computer is operatively connected to the generator for controlling the generator to change at least one of the preselected wavelength, the preselected amplitude, and the preselected polarization. The computer may include means for automatically varying the preselected wavelength, the preselected amplitude, and/or the preselected polarization in accordance with a preprogrammed sequence.

A medical tissue investigation system comprises, in accordance with another conceptualization of the present invention, a generator for generating electromagnetic energy having a predetermined plurality of wavelengths, a modulator operatively connected to the generating means for modulating at least one of the wavelengths, a transmitter for transmitting the energy including the modulated wavelength through the patient to the predetermined point, and a detector for automatically detecting electromagnetic radiation emitted from organic cellular material at the predetermined point in response to excitation of the cellular material by the energy including the modulated wavelength upon transmission thereof to the predetermined point, the step of detecting including the step of filtering out extraneous background noise in incoming electromagnetic radiation having the one of the wavelengths. A computer is operatively connected to the detector for automatically determining a spectral output of the organic cellular material from electromagnetic radiation received from the predetermined point through the patient during the step of detecting.

A system and a technique in accordance with the present invention obtains diagnostic information as to internal tissues of a patient in a relatively non-invasive way. No incisions are necessary. No conventional biopsy is performed.

DETAILED DESCRIPTION

Figure 1:
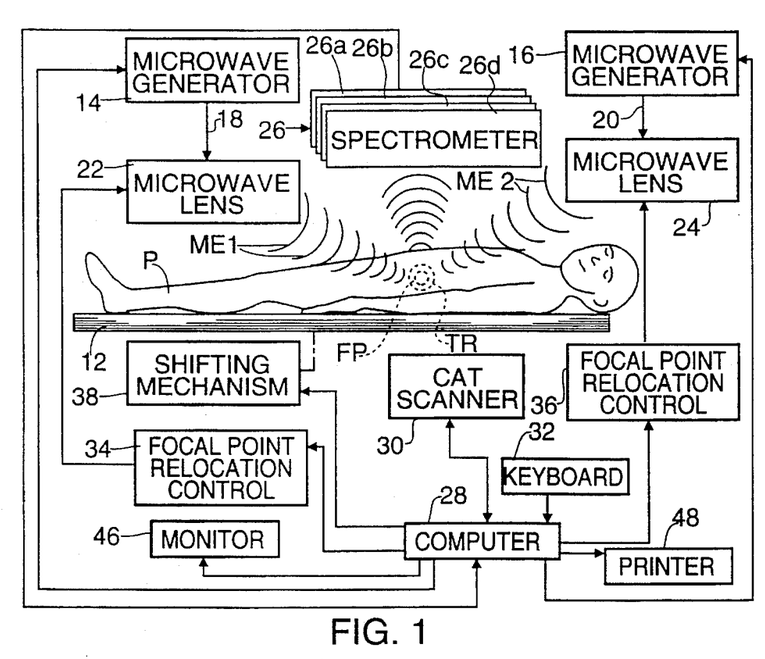
FIG. 1 is a block diagram of a medical investigative or diagnosis type system in accordance with the present invention.

As illustrated in FIG. 1, a medical diagnosis system comprises a support 12 for supporting a patient P in a predetermined position and a plurality of microwave radiation generators 14 and 16 for generating electromagnetic energy having a predetermined range of wavelengths in the microwave region of the electromagnetic spectrum. Each microwave radiation generator 14 and 16 is connected via a wave guide 18 or 20 to a respective focusing device or microwave lens 22 or 24. Lenses 22 and 24 are disposed between the respective radiation generator 14 and 16 and patient support 12 for focusing microwaves ME1 and ME2 at a predetermined focal point FP internal to a target region TR inside patient P.

A photodetector assembly or spectrometer assembly 26 comprising a plurality of individual photodetectors or scanning spectrometers 26a, 26b, 26c, 26d is disposed proximately to patient support 12 for detecting electromagnetic radiation ER from the patient P. Radiation ER is emitted from organic cellular material at predetermined focal point FP in response to excitation of the cellular material by the microwaves ME1 and ME2. Generally, molecules in a limited number of cells in target region TR are excited by the incoming microwaves ME1 and ME2 to photoluminesce and emit radiation ER. A part of radiation ER escapes through overlying organic tissues of the patient P and is detectable by photodetector assembly or spectrometer assembly 26.

The cells containing the excited molecules are generally destroyed upon excitation by microwaves EM1 and EM2. However, the focus is controlled by lenses 22 and 24 to limit the area which is affected in any one excitation step. The size of focal point FP is also limited in part by pulsing the microwave energy.

A computer 28 is operatively connected to photodetector assembly 26 for analyzing the signals from the photodetector assembly to ascertain a spectral output of the organic cellular material which luminesced at focal point FP. Inasmuch as the spectral content Of the escaping radiation ER is differentially modified by the tissues through which the radiation passes, computer 28 must be programmed to approximate the original spectral content of the radiation emitted by the excited molecular or cellular material at focal point FP. To that end, computer 28 is previously programmed to store known absorption spectra for different kinds of tissue. In addition, computer 28 is provided with three-dimensional structural data as to the organs of patient P surrounding target region TR. That structural data is provided by a CAT scanner or NMR imaging apparatus 30 connected to computer 28. From the kinds and thicknesses of the tissues between focal point FP and a respective unit 26a, 26b, 26c, or 26d of photodetector assembly 26, computer 28 is able to reconstruct the original spectral content of the radiation ER emitted in a photoluminescence process by the excited organic material at focal point FP.

Computer 28 is connected to generators 14 and 16 for controlling such parameters as the rate of pulsing, the interpulse interval, the pulse duration and the intensity of the radiation. These parameters may be preset by an operator via a keyboard 32. In addition, the spectral range of the microwave energy produced generators 14 and 16 may be adjusted in response to signals from computer 28. Furthermore, computer 28 may be instructed via keyboard 32 to automatically vary the microwave output of generators 14 and 16 during a single diagnostic procedure on patient P.

It is to be noted that a plurality of microwave generators 14 and 16, with their respective focusing lenses 22 and 24, are provided in part to minimize the amount of radiation absorbed by tissues outside of target region TR. It is only at focal point FP that the microwave energy is sufficiently intense to cause photoluminescence with its concomitant destruction of biological cells.

Target region TR is predetermined through computer-aided tomography as implemented by CAT scanner 30 or through the use of an NMR imaging apparatus. The location of target region TR may be manually input to computer 28. Alternatively, computer 28 is connected to CAT scanner or NMR imaging apparatus 30, whereby the location of target region TR may be automatically fed therefrom to computer 28.

As further illustrated in FIG. 1, computer 28 is connected to a pair of focal point relocation control units 34 and 36 in turn connected to respective microwave lenses 22 and 24. In response to signals from computer 28, control units 34 and 36 can continually or periodically change the location of focal point FP in accordance with a preprogrammed sequence, thereby to enabling a continual or repeatable luminescent emission of radiation from cellular or organic material within target region TR. This procedure increases the amount of radiation collected by photodetector assembly 26, thereby facilitating a determination of the spectral emission by target region TR. Within limits imposed, for example, by the size of target region TR, the microwave excitation and photoluminescence process can be continued until computer 28 has acquired sufficient data to diagnose the tissues of target region TR, for example, as malignant or benign.

As an alternative or supplement to relocation control units 34 and 36, a shifting mechanism 38 is connected to patient support 12 and computer 28 for shifting the position of the patient P under the control of computer 28, thereby changing the location of the focal point FP relative to the patient.

Figure 2:
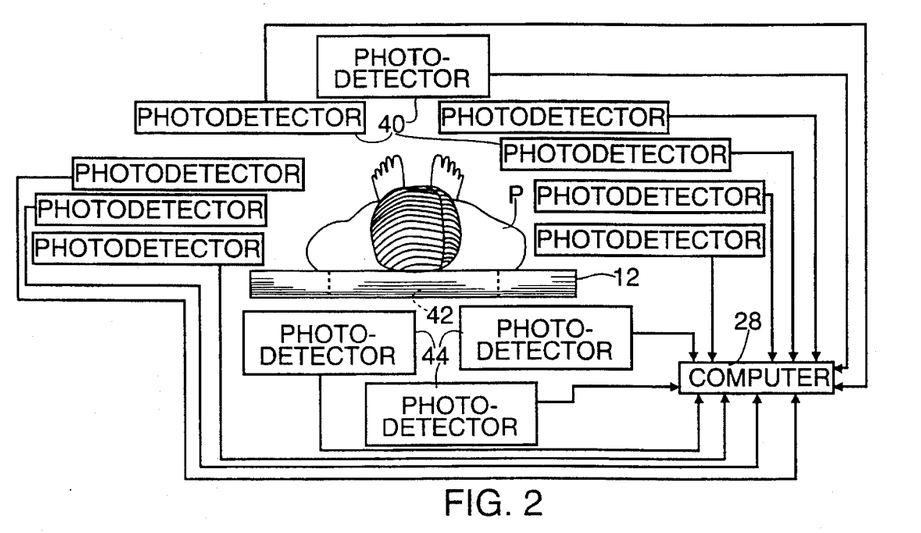
FIG. 2 is a block diagram showing details of a preferred embodiment of the medical investigative or diagnosis system of FIG. 1.

As depicted in FIG. 2, photodetector assembly 26 may include an array of individual photodetectors 40 disposed in an arc or annular array about patient support 12. To increase the amount of collectible data, support 12 may be formed with an opening 42 so that photodetectors 44 may be disposed below patient P.

Computer 28 is connected to peripheral output devices such as a monitor 46 and a printer 48 (FIG. 1) for communicating the results of spectral analyses and automatic diagnoses to a user.

Figure 3:
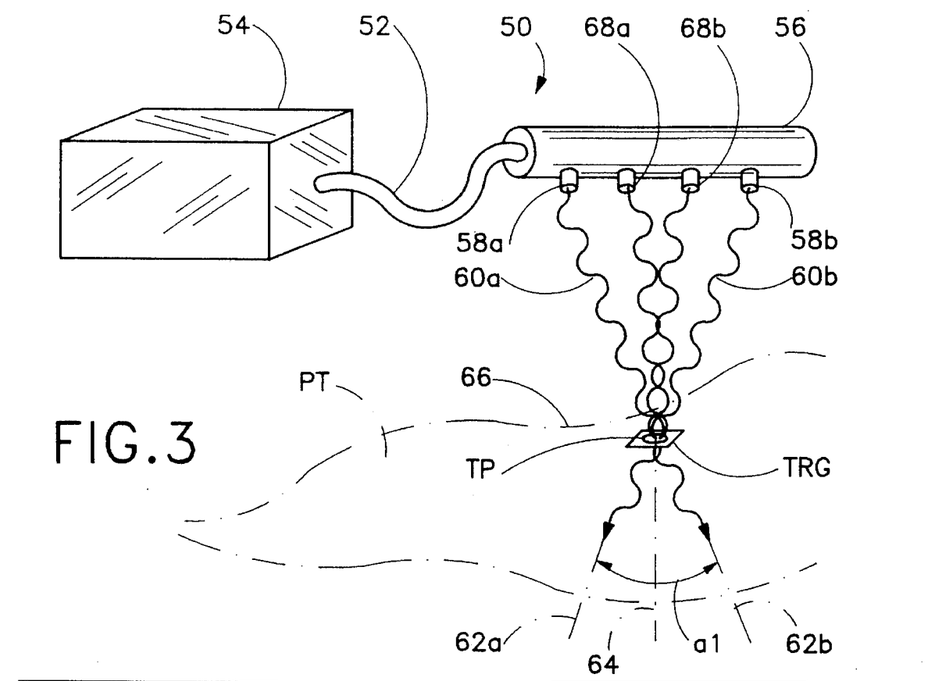
FIG. 3 is a schematic perspective view of another medical investigative or diagnostic type medical system in accordance with the present invention.

As illustrated in FIG. 3, a medical tissue investigation system comprises a hand held unit or portable transceiver device 50 connected via a waveguide cable 52 to a main housing unit 54. Hand held unit 50 includes a casing 56 provided with a plurality of spaced output ports 58a and 58b for the transmission of collimated electromagnetic test radiation 60a and 60b along respective lines 62a and 62b extending through a patient PT. Lines 62a and 62b are coplanar and intersect one another at a predeterminable test or target point TP inside a test region TRG. Lines 62a and 62b extend at variable angle a1 with respect to one another, as described below. Angle a1 may change so that test point TP moves along a line 64. Line 64 will coincide with line 62a or 62b in the event that the direction of transmission of radiation 60a or 60b remains constant while the direction of transmission of radiation 60b or 60a varies to change angle a1. Generally, line 64 extends perpendicularly to an external surface of patient PT at a point 66 indicated by a patient as being the location of pain.

Casing 56 is provided further with a plurality of input ports 68a and 68b containing respective photodetectors 70a and 70b (FIG. 4) or optical elements (not shown) for transmitting incoming radiation to the photodetectors.

Figure 4:
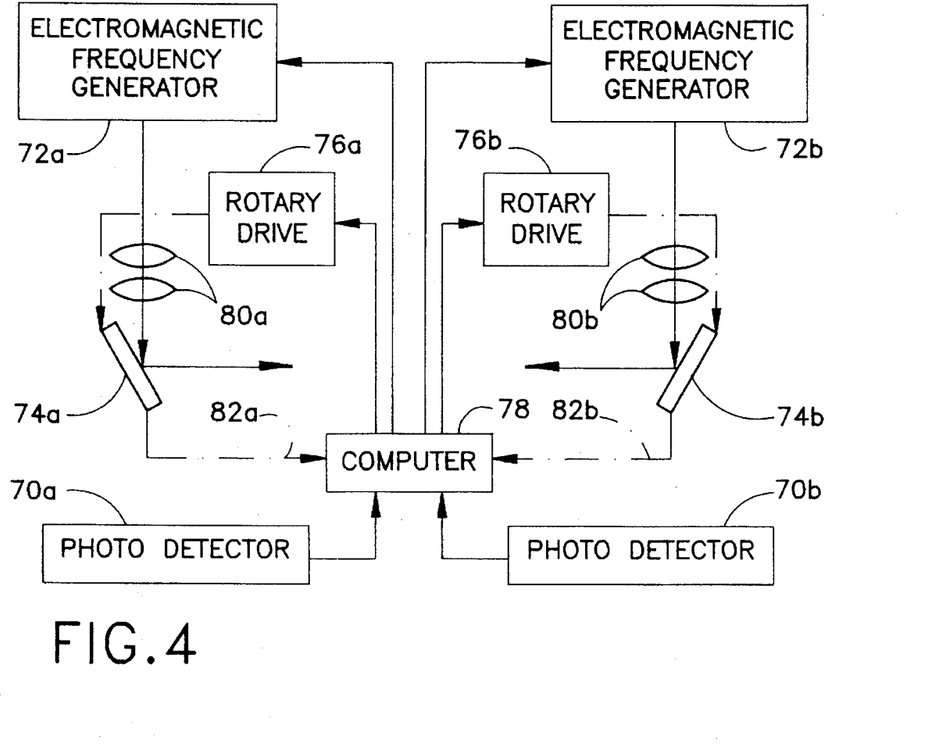
FIG. 4 is a block diagram of functional components of FIG. 3.

As illustrated in FIG. 4, the medical tissue investigation system of FIG. 3 further comprises a first generator 72a for generating electromagnetic energy or radiation 60a having a predetermined first frequency. Generator 72a is disposed in housing unit 54 and is connected to a first directional transmitter 74a disposed, for example, at output port 58a for transmitting the first frequency along line 62a. A second generator 72b, also disposed in housing unit 54, generates electromagnetic energy or radiation 60b having a predetermined second frequency different from the frequency of energy or radiation 60a. A second directional transmitter 74b is disposed at output port 58b in casing 56 for transmitting the second frequency 60b along line 62b.

As illustrated schematically in FIG. 4, directional transmitters 74a and 74b may take the form of mirrors which are provided with respective rotary drives 76a and 76b for turning the mirrors to vary the directions of propagation of frequencies or radiation 60a and 60b (FIG. 3), i.e., for varying the orientations of lines 62a and 62b relative to casing 56 and relative to the patient PT.

Photoelectric detector or photodetectors 70a and 70b are arranged in an array, e.g., on casing 56, for automatically detecting electromagnetic radiation emitted from organic cellular material in region TRG in response to excitation of the cellular material by the first frequency or radiation 60a and the second frequency or radiation 60b upon simultaneous irradiation of the tissues at point TP by frequencies 60a and 60b. As illustrated in FIG. 4, a computer 78 is operatively connected to photodetectors 70a and 70b for automatically determining a spectral output of the organic cellular material in region TRG from electromagnetic radiation received from the predetermined point TP through the patient PT.

Computer 78 is operatively connected to frequency generators 72a and 72b for changing the output frequencies thereof in a predetermined or preprogrammed sequence. Thus, the system of FIGS. 3 and 4 is able to subject any test or target point TP to a multitude of different frequencies. Computer 78 is also connected to rotary drives 76a and 76b for controlling the operation thereof. Accordingly, computer 78 determines the locations of successive test points, as well as the test frequencies to which the cellular material at the test or target points TP are subjected.

Electromagnetic frequency generators 72a and 72b may be laser sources producing output radiation transmitted along optical fibers of cable 52 (FIG. 3) to collimating lenses 80a and 80b, e.g., in casing 54, upstream of directional mirrors 74a and 74b. At any one time, generators 72a and 72b may produce the same frequency. In that case, radiation 60a and 60b combine at the test or target point TP to provide a sufficient intensity for stimulating or exciting organic molecules within test region TRG. The location of test region TRG or test point TP is determinable by a scanner such as a CAT scanner (FIG. 1) or a magnetic resonance imaging apparatus (not shown). Alternatively, an optical scanner with pattern recognition (see FIG. 5) may function in combination with an ultrasonic or infrared distance scanner (FIG. 5) to automatically determine the location of test region TRG or test point TP.

In an alternate mode of operation of the medical testing and diagnostic system of FIGS. 3 and 4, computer 78 controls generators 72a and 72b to produce radiation 60a and 60b of different frequencies or wavelengths. The spectra of organic tissues in test region TRG excited by such multiple frequencies or wavelengths will differ from the spectra of tissues subjected to either frequency by itself.

The transmission of multiple test frequencies, which impinge upon the same organic tissues only at the test or target point PT, can provide information to computer 78 as to the location of the organic tissues, as described in greater detail hereinafter with reference to FIG. 5. Computer 78 is provided with feedback 82a and 82b as to the angles of directional transmission mirrors 76a and 76b, thereby enabling computation of the location of test region TRG.

Figure 5:
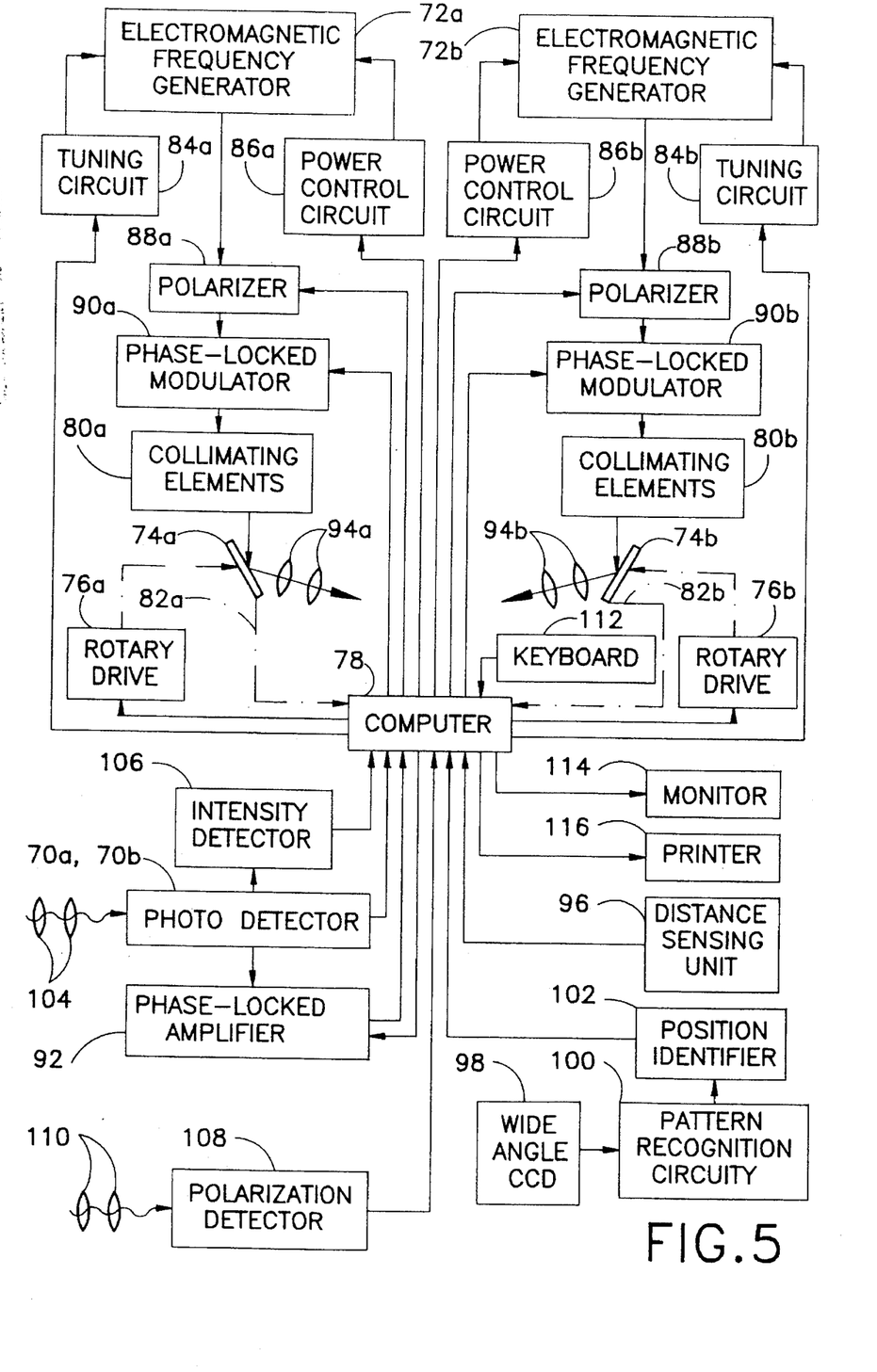
FIG. 5 is a block diagram showing a modified embodiment of the medical investigative or diagnostic type medical system of FIGS. 3 and 4.

Components in FIG. 5 which are the same as components in FIG. 4 bear the same reference designations. FIG. 5 shows additional componentry for enhancing the operation of the medical investigative and diagnostic system of FIGS. 3 and 4.

As illustrated in FIG. 5, computer 78 is connected at outputs to tuning circuits 84a and 84b which are in turn connected to respective generators 72a and 72b for varying, in response to control signals from computer 78, the frequencies of the radiation 60a and 60b (FIG. 3) produced by generators 72a and 72b. In addition, computer 78 is linked at outputs to power control circuits 86a and 86b which in turn are coupled to generators 72a and 72b for varying the intensity or amplitude of radiation 60a and 60b produced by generators 72a and 72b pursuant to signals from computer 78.

Polarizers 88a and 88b are disposed at the outputs of generators 72a and 72b for varying the polarization of the radiation produced by the generators. Polarizers 88a and 88b are adjustable in response to signals from computer 78. Polarizers 88a and 88b may incorporate componentry for controlling the phase of the generated test frequencies in response to signals from computer 78.

As further illustrated in FIG. 5, phase locked modulators 90a and 90b are provided at the outputs of generators 72a and 72b for modulating the output frequencies or radiation thereof in response to signals from computer 78. Modulators 90a and 90b may operate electrically via modulation of an optical crystal, mechanically via a gating device or chopper, or electronically in the case of microwave emissions. Modulators 90a and 90b cofunction with a demodulating phase-locked amplifier 92 to filter out extraneous background noise in incoming electromagnetic radiation generated by organic matter in response to the output frequencies or wavelengths of generators 72a and 72b. Computer 78 is operatively linked to modulators 90a and 90b and to amplifier 92 for possibly modifying the modulating signal.

Modulated frequencies or waveforms from modulators 90a and 90b are collimated by elements 80a and 80b and directed by mirrors 74a and 74b to a selected target region TRG (FIG. 3). Supplementary focusing elements 94a and 94b may be provided at output ports 58a and 58b (FIG. 3) for focusing the modulated frequencies 60a and 60b at target point TP. Focusing elements 94a and 94b may be controlled by computer 78 to adjust the target point TP.

It is to be noted that the frequencies produced by generators 72a and 72b for exciting target organic tissues span from the ultraviolet through the visible and infrared to microwave frequencies at approximately 30 GHz. It is to be noted further that more than two output ports 58a and 58b may be provided on casing 56. Multiple output ports may be connected to the same frequency generator 72a or 72b. Moreover, the componentry of FIG. 5 may be provided in a stationary installation where hand held casing 56 (FIG. 3) is omitted.

As indicated schematically by dot-dash lines at 82a and 82b, signal generators may be operatively connected to directional mirrors or transmitters 74a and 74b for producing electrical signals encoding a first angle identifying line 62a (FIG. 3) and a second angle identifying line 62b. Computer 78 is operatively connected to the signal generators for computing a location of test or target point TP relative to patient PT in response to the electrical signals.

To further facilitate this locating process, a distance sensing unit or scanner 96 is disposed in hand held unit 50 and is connected to computer 78. Distance sensing unit or scanner 96 incorporates ultrasonic or infrared distance sensors (not separately illustrated) to automatically determine the distance of the patient PT from casing 56. Concomitantly, computer 78 is able to determine the location of test region TRG or test point TP within the patient from the information regarding the location of the patient relative to hand held unit 50 and the location of the test region TRG relative to the hand held unit.

Further locating componentry in the form of a wide angle camera (e.g., a charge coupled device or CCD) 98 may be provided on hand held unit 50. Camera 98 is connected to a pattern recognition circuit 100 and a position identification component 102 which cofunction to determine over what part of the patient PT point 66 is located. Pattern recognition circuit 100 and position identification component 102 are incorporated into or connected to computer 78 for facilitating the locating function thereof.

In the system of FIG. 5, computer 78 controls generator 72a and/or generator 72b via tuning circuit 84a or 84b, via power control circuit 861 or 86b for generating electromagnetic energy characterized by a preselected wavelength and a preselected amplitude. In addition, computer 78 can control the polarization of the electromagnetic radiation via polarizer 88a or 88b. Any one or all of these radiation parameters can be changed in a preprogrammed sequence to investigate the spectral response of organic tissues in test or target region TRG (FIG. 3). (It is to be noted that the term "spectral response" as used herein is intended to encompass the entire response of organic tissues in a test region TRG, including frequency or wavelength, amplitude or intensity, phase, polarization, fluorescent delay, etc.) In addition, by controlling the orientation of directional mirrors or transmitters 74a and 74b (and optionally, the orientations of focusing elements 94a and 94b), computer 78 can test organic spectral responses at different test points TP.

As further illustrated in FIG. 5, radiation collecting elements 104 are disposed upstream of photodetectors 70a, 70b for enhancing the sensitivity thereof. On a downstream or output side, photodetectors 70a, 70b are connected to an intensity detector 106 which measures the intensity of different wavelengths detectable by photodetectors 70a, 70b. Intensity detector 106 is connected to computer 78 for informing that unit of intensity or amplitude measurement results. Computer 78 may select intensity or amplitude measurement results which conform to a modulation signal, as sensed by amplifier 92. In additional, a polarization detector or analyzer 108 with concentrating input elements 110 is connected to an input of computer 78 for providing the computer with data pertaining to the polarization characteristics of incoming radiation arriving from irradiated regions of the patient.

The transmission of multiple test frequencies, which impinge upon the same organic tissues only at the test or target point PT, can provide information to computer 78 as to the location of the organic tissues, as described in greater detail hereinafter with reference to FIG. 5. Computer 78 is provided with feedback 82a and 82b as to the angles of directional transmission mirrors 76a and 76b, thereby enabling computation of the location of test region TRG.

Components in FIG. 5 which are the same as components in FIG. 4 bear the same reference designations. FIG. 5 shows additional componentry for enhancing the operation of the medical investigative and diagnostic system of FIGS. 3 and 4.

As illustrated in FIG. 5, computer 78 is connected at outputs to tuning circuits 84a and 84b which are in turn connected to respective generators 72a and 72b for varying, in response to control signals from computer 78, the frequencies of the radiation 60a and 60b (FIG. 3) produced by generators 72a and 72b. In addition, computer 78 is linked at outputs to power control circuits 86a and 86b which in turn are coupled to generators 72a and 72b for varying the intensity or amplitude of radiation 60a and 60b produced by generators 72a and 72b pursuant to signals from computer 78.

Polarizers 88a and 88b are disposed at the outputs of generators 72a and 72b for varying the polarization of the radiation produced by the generators. Polarizers 88a and 88b are adjustable in response to signals from computer 78. Polarizers 88a and 88b may incorporate componentry for controlling the phase of the generated test frequencies in response to signals from computer 78.

As further illustrated in FIG. 5, phase locked modulators 90a and 90b are provided at the outputs of generators 72a and 72b for modulating the output frequencies or radiation thereof in response to signals from computer 78. Modulators 90a and 90b may operate electrically via modulation of an optical crystal, mechanically via a gating device or chopper, or electronically in the case of microwave emissions. Modulators 90a and 90b cofunction with a demodulating phase-locked amplifier 92 to filter out extraneous background noise in incoming electromagnetic radiation generated by organic matter in response to the output frequencies or wavelengths of generators 72a and 72b. Computer 78 is operatively linked to modulators 90a and 90b and to amplifier 92 for possibly modifying the modulating signal.

Modulated frequencies or waveforms from modulators 90a and 90b are collimated by elements 80a and 80b and directed by mirrors 74a and 74b to a selected target region TRG (FIG. 3). Supplementary focusing elements 94a and 94b may be provided at output ports 58a and 58b (FIG. 3) for focusing the modulated frequencies 60a and 60b at target point TP. Focusing elements 94a and 94b may be controlled by computer 78 to adjust the target point TP.

It is to be noted that the frequencies produced by generators 72a and 72b for exciting target organic tissues span from the ultraviolet through the visible and infrared to microwave frequencies at approximately 30 GHz. It is to be noted further that more than two output ports 58a and 58b may be provided on casing 56. Multiple output ports may be connected to the same frequency enerator 72a or 72b. Moreover, the componentry of FIG. 5 may be provided in a stationary installation where hand held casing 56 (FIG. 3) is omitted.

As indicated schematically by dot-dash lines at 82a and 82b, signal generators may be operatively connected to directional mirrors or transmitters 74a and 74b for producing electrical signals encoding a first angle identifying line 62a (FIG. 3) and a second angle identifying line 62b. Computer 78 is operatively connected to the signal generators for computing a location of test or target point TP relative to patient PT in response to the electrical signals.

To further facilitate this locating process, a distance sensing unit or scanner 96 is disposed in hand held unit 50 and is connected to computer 78. Distance sensing unit or scanner 96 incorporates ultrasonic or infrared distance sensors (not separately illustrated) to automatically determine the distance of the patient PT from casing 56. Concomitantly, computer 78 is able to determine the location of test region TRG or test point TP within the patient from the information regarding the location of the patient relative to hand held unit 50 and the location of the test region TRG relative to the hand held unit.

Further locating componentry in the form of a wide angle camera (e.g., a charge coupled device or CCD) 98 may be provided on hand held unit 50. Camera 98 is connected to a pattern recognition circuit 100 and a position identification component 102 which cofunction to determine over what part of the patient PT point 66 is located. Pattern recognition circuit 100 and position identification component 102 are incorporated into or connected to computer 78 for facilitating the locating function thereof.

In the system of FIG. 5, computer 78 controls generator 72a and/or generator 72b via tuning circuit 84a or 84b, via power control circuit 861 or 86b for generating electromagnetic energy characterized by a preselected wavelength and a preselected amplitude. In addition, computer 78 can control the polarization of the electromagnetic radiation via polarizer 88a or 88b. Any one or all of these radiation parameters can be changed in a preprogrammed sequence to investigate the spectral response of organic tissues in test or target region TRG (FIG. 3). (It is to be noted that the term "spectral response" as used herein is intended to encompass the entire response of organic tissues in a test region TRG, including frequency or wavelength, amplitude or intensity, phase, polarization, fluorescent delay, etc.) In addition, by controlling the orientation of directional mirrors or transmitters 74a and 74b (and optionally, the orientations of focusing elements 94a and 94b), computer 78 can test organic spectral responses at different test points TP.

As further illustrated in FIG. 5, radiation collecting elements 104 are disposed upstream of photodetectors 70a, 70b for enhancing the sensitivity thereof. On a downstream or output side, photodetectors 70a, 70b are connected to an intensity detector 106 which measures the intensity of different wavelengths detectable by photodetectors 70a, 70b. Intensity detector 106 is connected to computer 78 for informing that unit of intensity or amplitude measurement results. Computer 78 may select intensity or amplitude measurement results which conform to a modulation signal, as sensed by amplifier 92. In additional, a polarization detector or analyzer 108 with concentrating input elements 110 is connected to an input of computer 78 for providing the computer with data pertaining to the polarization characteristics of incoming radiation arriving from irradiated regions of the patient.

In this regard, it is to be noted that photodetectors 70a, 70b may be individually tuned to respective frequencies. Photodetectors 70a, 70b, together with intensity detector 106 and computer 78, thus cofunction as a spectrometer for determining the spectral output or a respective tissue sample in a patient PT.

With the help of input from photodetectors 70a, 70b, intensity detector 106, polarization detector 108 and amplifier 92, computer 78 automatically analyzes electromagnetic radiation received from test or target point TP through the patient PT and determines a spectral radiation output of organic cellular material. The spectral output is characterized by wavelength, amplitude, and polarization (and possibly phase).

As discussed hereinabove with reference to FIGS. 3 and 4, the investigative system may transmit two different frequencies through a patient to a target point TP or test region TRG. The two frequencies may belong to respective wavelength packets which are spectrally spaced from one another, or only overlap to a limited extent. Each frequency or radiation beam 60a and 60b is transmitted along its respective line or path 62a and 62b. Lines 62a and 62b extend through the patient at angle a1 relative to one another. The angle a1 is determinable by computer 78 by input 82a and 82b regarding the orientations of directional mirrors or transmitters 74a and 74b. Frequencies or radiation beams 60a and 60b are transmitted simultaneously.

To separate out spectral response patterns originating in test region TRG from electromagnetic emissions from organic material outside of the test region but inside the patient, a first calibrating scan is undertaken with frequency or radiation 60a transmitted along line 62a and a second calibrating scan is undertaken with frequency or radiation beam 60b transmitted along line 62b. Computer 78 analyzes and registers the results, which are subsequently screened or subtracted out from the spectral responses detected upon the simultaneous irradiation of test region TRG with the two test frequencies or wavelength packets.

One mode of operation of the system of FIG. 5 is described hereinabove with reference to FIG. 3. Pursuant to that mode of operation, electromagnetic radiation 60a (FIG. 3) of the first frequency and electromagnetic radiation 60b of the second frequency are concentrated at a series of points within patient PT. The points may be disposed along line 64 extending through the patient. Generally, where the patient points to a region of localized pain at 66, line 64 extends generally perpendicularly to patient's skin surface at point 66 indicated by the patient. Test line 64 may coincide with a line of radiation transmission 62a or 62b. For example, in the former case, the first frequency or radiation beam 60a is transmitted along line 62a during the testing procedure, while the second frequency or radiation beam 60b is transmitted along a series of second lines, each such second line being oriented at a different angle a1 relative to line 62a, thereby enabling irradiation of a series of different test points TP with energy of the first frequency and the second frequency. Where both lines 62a and 62b change, line 64 is separate and distinct from both lines 62a and 62b. The testing sequence may have any predetermined order. For instance, it is possible that the test points occur randomly throughout a region of the patient, directional mirrors 74a and 74b being pivoted in accordance with a random preprogrammed sequence.

The principle underlying this methodology is that the spectral output of a particular organic molecule, and or atoms included in that molecule, will change depending on the multiple excitation frequencies used. Thus, molecules or a certain kind located at points irradiated by only one of the two frequencies will have a different spectral output than those molecules of the same kind located at the commonly irradiated (predetermined) point. This difference enables a differentiation of tissue responses in accordance with tissue locations.

It is understood that during an initial phase of usage of the above-described medical investigative and diagnostic systems, data is gathered as to spectral responses. This data is correlated with histological, cytological and physiological characteristics of the irradiated tissues which are determined from other, known techniques. From information acquired during this initial phase, a second generation investigative and diagnostic unit can be constructed, using the same components as described hereinabove. In addition, the investigative and diagnostic unit will include a keyboard 112 (FIG. 5) connected to computer 78 for instructing computer 78 to possibly select among a different preprogrammed sequences or to modify a sequence pursuant to externally obtained information. Output components such as a monitor 114 or a printer 116 are connected to computer 78 for advising an operator as to the results of spectral response investigations. Comparing spectral response patterns obtained from a particular patient with internally stored spectral response patterns previously obtained from hundreds, if not thousands, of other patients, computer 78 may provide a diagnosis via monitor 114 or printer 116. For example, where monitor 114 is provided on hand held unit 50, a diagnosis on monitor might read "gallstones" or "liver abscess" or "liver cancer." Diagnosable conditions will depend on which conditions are correlated with molecules having spectral response patterns detectable as described herein.

As discussed above, a single test point TP is subjected to different combinations of test frequencies. This enables computer 78 to determine spectral response characteristics associated with different types of molecules at the test point(s). The different molecules may in turn be associated with different tissue conditions. For example, calcified deposits (stones), cancerous tissues, abscess fluid, etc., all have characteristic agglomerations of molecules having their own spectral response patterns.

It is to be noted that irradiation of a test or target point inside a patient with multiple frequencies may be accomplished by the apparatus of FIG. 1. In that case, generators 14 and 16 produce electromagnetic radiation (e.g., microwave, near millimeter, infrared, optical or ultraviolet) of different frequencies. More particularly, each generator 14 and 16 produces radiation having a respective range of frequencies to form a respective wavelength packet. The different frequencies are concentrated at the predetermined test or target point FP by respectively focusing the first frequency and/or the second frequency at the predetermined point. The irradiating energy is not collimated but rather transmitted in a beam which converges to the predetermined test or target point.

The information collected by computer 78 during an investigative procedure includes more than a pure spectral response. As discussed above, intensity and polarization data may be useful in eventually identifying the type of tissues at a test point TP internal to a patient. All this information is collated by computer 78. The collation programming may take the form of a well known type of multidimensional mathematical analysis wherein the different individual measured characteristics (frequencies, intensities, polarization, etc.) are each associated with a coordinate axis of an analytical multidimensional space. Each test point in each patient tested thus constitutes a point in the multidimensional space. Upon the collection of hundreds or thousands of test points, all plotted in the multi-dimensional space, and the association of groups of tested points with different known therapeutic conditions, so-called decision boundaries are mathematically derived. The decision boundaries separate subsets in the multidimensional space which correspond to respective, different medical conditions. Thus, upon determination of the response of organic tissues in a new test region, computer 78 may compare the multidimensional analytical point with the collated multidimensional data to determine whether the newly measured response belongs to an identified subset of the multidimensional space.

Other data which may be collected by a medical investigative and diagnostic system as described herein includes delayed fluoresence and changes in phase. In addition, the patient may be subjected to types of energy other than electromagnetic radiation to determine possible changes in the spectral response pattern. Such energies include ultrasonic, infrasonic, and radio-emitting chemical compositions. Each test point TP is subjected to one or more frequencies or radiation beams 60a, 60b while the tissue in the respective test region TRG is subjected to one or more of these additional energies. Each of these supplemental energies expands the dimensions, i.e., increases the number of coordinate axes, of the analytical multidimensional space and thus provides further information for facilitating the distinguishing of one type of organic tissue from another.

It is to be understood that the medical investigative and diagnostic system of FIG. 5 may be used in conjunction with a wireless imaging device such as a CAT scanner or an MRI apparatus. That wireless imaging device is used in part to ascertain the location of test point TP relative to the subjects internal anatomy.

The componentry of a medical investigative and diagnostic system in accordance with the present invention may be used for medical treatment. For example, once the spectral response of any particular tissue type is determined, so that the absorption frequencies of key molecules in the tissue are known, those frequencies may be transmitted in increased intensity to the identified test region to destroy the target molecules and concomitantly disrupt the encompassing cells and tissues. For example, tumors may be destroyed, as well as infectitious bacteria or fungi.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are preferred by way of example to facilitate comprehension of the invention and should not be construed to limit the scope thereof.

What is claimed is:

1. A medical tissue investigation method comprising the steps of:

generating electromagnetic energy having a predetermined first frequency;

transmitting electromagnetic energy of said first frequency along a predetermined first line extending through a patient;

also generating electromagnetic energy having a predetermined second frequency different from said first frequency;

transmitting electromagnetic energy of said second frequency along a predetermined second line extending through the patient at a predetermined angle relative to said first line, said second line intersecting said first line at one predetermined point inside the patient, said steps of transmitting being performed simultaneously;

automatically detecting electromagnetic radiation emitted from organic cellular material at said predetermined point in response to excitation of said cellular material by electromagnetic energy of said first frequency and electromagnetic energy of said second frequency upon simultaneous irradiation of said predetermined point by electromagnetic energy of said first frequency and electromagnetic energy of said second frequency; and automatically determining a spectral output of said organic cellular material from electromagnetic radiation received from said predetermined point through the patient during said step of detecting.

2. The method defined in claim 1, further comprising the steps of:

again generating electromagnetic energy having said predetermined first frequency;

again transmitting electromagnetic energy of said first frequency along said predetermined first line extending through the patient;

generating electromagnetic energy having a predetermined third frequency;

transmitting electromagnetic energy of said third frequency along a predetermined third line extending through the patient at a predetermined angle relative to said first line, said third line intersecting said first line at said predetermined point inside the patient, said step of transmitting said electromagnetic energy of third frequency being performed simultaneously with said step of again transmitting electromagnetic energy of said first frequency;

again automatically detecting electromagnetic radiation emitted from said organic cellular material at said predetermined point in response to excitation of said cellular material by electromagnetic energy of said first frequency and electromagnetic energy of said third frequency upon simultaneous irradiation of said predetermined point by electromagnetic energy of said first frequency and electromagnetic energy of said third frequency; and again automatically determining a spectral output of said organic cellular material from electromagnetic radiation received from said predetermined point through the patient during said step of again automatically detecting.

3. The method defined in claim 1, further comprising the steps of:

directing electromagnetic energy of said second frequency along a predetermined third line extending through the patient at another predetermined angle relative to said first line, said third line intersecting said first line at an additional predetermined point inside the patient, said step of directing being performed simultaneously with said step of transmitting electromagnetic energy of said first frequency;

again automatically detecting electromagnetic radiation emitted from said organic cellular material at said additional predetermined point in response to excitation of said cellular material by electromagnetic energy of said first frequency and electromagnetic energy of said second frequency upon simultaneous irradiation of said additional predetermined point by electromagnetic energy of said first frequency and electromagnetic energy of said second frequency; and again automatically determining a spectral output of said organic cellular material from electromagnetic radiation received from said predetermined point through the patient during said step of again automatically detecting.

4. The method defined in claim 1 wherein said second frequency has a given phase, a given amplitude and a given polarization, further comprising the steps of:

generating electromagnetic energy having said predetermined second frequency, a selected phase, a selected amplitude, and a selected polarization, at least one of said selected phase, said selected amplitude, and said selected polarization being different from said given phase, said given amplitude and said given polarization, respectively;

transmitting electromagnetic energy of said second frequency with said selected phase, said selected amplitude, and said selected polarization along said second line through the patient simultaneously with a transmission of electromagnetic energy of said first frequency along said first line;

again automatically detecting electromagnetic radiation emitted from organic cellular material at said predetermined point in response to excitation of said cellular material by electromagnetic energy of said first frequency and electromagnetic energy of said second frequency upon simultaneous irradiation of said predetermined point by electromagnetic energy of said first frequency and electromagnetic energy of said second frequency with said selected phase, said selected amplitude, and said selected polarization; and again automatically determining a spectral output of said organic cellular material from electromagnetic radiation received from said predetermined point through the patient during said step of detecting.

5. The method defined in claim 1 wherein said steps of generating and also generating include the steps of operating a first laser to generate electromagnetic energy of said first frequency and operating a second laser to generate electromagnetic energy of said second frequency, respectively.

6. The method defined in claim 1, further comprising the steps of:

producing electrical signals encoding a first angle identifying said first line and a second angle identifying said second line; and in response to said electrical signals, computing a location of said predetermined point relative to the patient.

7. The method defined in claim 1 wherein said steps of generating and also generating include the steps of collimating electromagnetic energy of said first frequency and collimating electromagnetic energy of said second frequency, respectively.

8. The method defined in claim 1, further comprising the step of modulating electromagnetic energy of at least one of said first frequency and said second frequency prior to the transmission thereof through the patient.

9. The method defined in claim 8 wherein said step of modulating includes the step of operating a phase locked modulator, further comprising the step of generating an electrical signal in response to said step of detecting, said step of determining including the step of processing said electrical signal, said step of generating including the step of operating a phase locked amplifier.

10. The method defined in claim 1, further comprising the step of varying at least one of said first frequency and said second frequency.

11. The method defined in claim 10 wherein said step of varying is automatically implemented in accordance with a preprogrammed sequence.

12. The method defined in claim 1, further comprising the step of holding a transceiver device by hand, transmission of electromagnetic energy of said first frequency and electromagnetic energy of said second frequency being from said transceiver device, said step of detecting including the step of operating a photoelectric transducer on said transceiver device.

13. The method defined in claim 1 wherein said steps of transmitting include the steps of transmitting electromagnetic energy of said first frequency in a narrow beam along said first line and transmitting electromagnetic energy of said second frequency in a narrow beam along said second line, respectively.

14. The method defined in claim 1, further comprising the steps of focusing electromagnetic energy of said first frequency and focusing electromagnetic energy of said second frequency at said predetermined point.

15. A medical tissue investigation method comprising the steps of:

generating electromagnetic energy characterized by a preselected wavelength, a preselected amplitude, and a preselected polarization;

concentrating said energy towards a predetermined point internal to a patient;

transmitting said energy through the patient to said predetermined point;

automatically detecting electromagnetic radiation emitted from organic cellular material at said predetermined point in response to excitation of said cellular material by said energy upon concentration thereof at said predetermined point; and automatically determining, from electromagnetic radiation received from said predetermined point through the patient during said step of detecting, a radiation output of said organic cellular material characterized by wavelength, amplitude, and polarization.

16. The method defined in claim 15, further comprising the step of varying at least one of said preselected wavelength, said preselected amplitude, and said preselected polarization.

17. The method defined in claim 16 wherein said step of varying is automatically implemented in accordance with a preprogrammed sequence.

18. The method defined in claim 15, further comprising the step of changing the location of said predetermined point in accordance with a preprogrammed sequence.

19. A medical tissue investigation method comprising the steps of:

generating electromagnetic energy having a predetermined plurality of wavelengths;

modulating at least one of said wavelengths;

transmitting said energy including the modulated wavelength through a patient to a predetermined point internal to the patient;

automatically detecting electromagnetic radiation emitted from organic cellular material at said predetermined point in response to excitation of said cellular material by said energy including the modulated wavelength upon transmission thereof to said predetermined point, said step of detecting including the step of filtering out extraneous background noise in incoming electromagnetic radiation having said one of said wavelengths; and automatically determining a spectral output of said organic cellular material from electromagnetic radiation received from said predetermined point through the patient during said step of detecting.

20. The method defined in claim 19 wherein said step of modulating includes the step of operating a phase locked modulator, said step of filtering including the step of operating a phase locked amplifier.

21. The method defined in claim 19, further comprising the step of varying said one of said wavelengths.

22. The method defined in claim 21 wherein said step of varying said one of said wavelengths is automatically implemented in accordance with a preprogrammed sequence.

23. The method defined in claim 19, further comprising the step of automatically changing the location of said predetermined point pursuant to a predetermined sequence.

24. The method defined in claim 19 wherein said step of changing is automatically implemented by transmitting said energy to another point internal to the patient and different from said predetermined point.

25. A medical tissue investigation method comprising the steps of:

generating electromagnetic energy having a predetermined plurality of wavelengths;

transmitting said energy through a patient to a predetermined point internal to the patient;

concentrating said energy at said predetermined point;

automatically determining the location of said predetermined point relative to the patient;

automatically detecting electromagnetic radiation emitted from organic cellular material at said predetermined point in response to excitation of said cellular material by said energy upon concentrating thereof at said predetermined point;

automatically determining a spectral output of said organic cellular material from electromagnetic radiation received from said predetermined point through the patient during said step of detecting; and correlating the determined spectral output of said organic cellular material with the location of said predetermined point relative to the patient.

26. The method defined in claim 25 wherein said step of determining the location of said predetermined point includes the step of operating a wireless imaging device.

27. The method defined in claim 25 wherein said step of determining the location of said predetermined point includes the step of automatically determining a direction of transmission of said energy through the patient.

28. The method defined in claim 25, further comprising the step of varying said wavelengths.

29. A medical tissue investigation system comprising:

first generating means for generating electromagnetic energy having a predetermined first frequency;

first directional transmission means for transmitting electromagnetic energy of said first frequency along a predetermined first line extending through a patient;

second generating means for generating electromagnetic energy having a predetermined second frequency different from said first frequency;

second directional transmission means for transmitting electromagnetic energy of said second frequency along a predetermined second line extending through the patient at a predetermined angle relative to said first line, said second line intersecting said first line at one predetermined point inside the patient;

detection means for automatically detecting electromagnetic radiation emitted from organic cellular material at said predetermined point in response to excitation of said cellular material by electromagnetic energy of said first frequency and electromagnetic energy of said second frequency upon simultaneous irradiation of said predetermined point by electromagnetic energy of said first frequency and electromagnetic energy of said second frequency; and computing means operatively connected to said detection means for automatically determining a spectral output of said organic cellular material from electromagnetic radiation received from said predetermined point through the patient, said computing means being operatively connected to at least one of said first generating means and said second generating means for controlling said one of said first generating means and said second generating means to change a respective one of said first frequency and said second frequency, said computing means being operatively connected to at least one of said first directional transmission means and said second directional transmission means for controlling said one of said first directional transmission means and said second direction transmission means to change a respective one of said first line and said second line.

30. The system defined in claim 29 wherein at least one of said first directional transmission means and said second directional transmission means includes means for changing said angle by changing a direction of a respective one of said first line and said second line.

31. The system defined in claim 29 wherein said second generating means includes means for changing at least one of an amplitude, a phase and a polarization of electromagnetic energy of said second frequency.

32. The system defined in claim 29 wherein at least one of said first generating means and said second generating means includes a laser for generating electromagnetic energy of a respective one of said first frequency and said second frequency.

33. The system defined in claim 29, further comprising signal generating means operatively connected to said first directional transmission means and said second directional transmission means for producing electrical signals encoding a first angle identifying said first line and a second angle identifying said second line, said computing means being operatively connected to said signal generating means for computing a location of said predetermined point relative to the patient in response to said electrical signals.

34. The system defined in claim 29 wherein at least one of said first generator means and said second generating means includes means for collimating electromagnetic energy of a respective one of said first frequency and said second frequency.

35. The system defined in claim 29, further comprising modulator means for modulating electromagnetic energy of at least one of said first frequency and said second frequency prior to the transmission thereof through the patient.

36. The system defined in claim 35 wherein said modulator means includes a phase locked modulator, said detection means including a phase locked amplifier for generating an electrical signal encoding incoming detected electromagnetic energy.

37. The system defined in claim 29, further comprising a portable transceiver device, said first direction transmission means and said second directional transmission means being disposed on said transceiver device, said detection means including a photoelectric transducer on said transceiver device.

38. A medical tissue investigation system comprising:

generating means for generating electromagnetic energy characterized by a preselected wavelength, a preselected amplitude, and a preselected polarization;

transmission means for transmitting said energy through a patient to a predetermined point internal to the patient;

detection means for automatically detecting electromagnetic radiation emitted from organic cellular material at said predetermined point in response to excitation of said cellular material by said energy upon concentration thereof at said predetermined point; and computing means operatively connected to said detection means for automatically determining, from electromagnetic radiation received from said predetermined point through the patient, a radiation output of said organic cellular material characterized by wavelength, amplitude, and polarization, said computing means being operatively connected to said generating means for controlling said generating means to change at least one of said preselected wavelength, said preselected amplitude, and said preselected polarization.

39. The system defined in claim 38 wherein said computing means includes means for automatically varying said at least one of said preselected wavelength, said preselected amplitude, and said preselected polarization in accordance with a preprogrammed sequence.

40. A medical tissue investigation system comprising:

generating means for generating electromagnetic energy having a predetermined plurality of wavelengths;

modulator means operatively connected to said generating means for modulating at least one of said wavelengths;

transmission means for transmitting said energy including the modulated wavelength through a patient to a predetermined point internal to the patient;

detection means for automatically detecting electromagnetic radiation emitted from organic cellular material at said predetermined point in response to excitation of said cellular material by said energy including the modulated wavelength upon transmission thereof to said predetermined point, said detection means including filtering means for filtering out extraneous background noise in incoming electromagnetic radiation having said one of said wavelengths; and computing means operatively connected to said detection means for automatically determining a spectral output of said organic cellular material from electromagnetic radiation received from said predetermined point through the patient.

41. The system defined in claim 40, wherein said modulator means includes a phase locked modulator, said detection means including a phase locked amplifier.

42. The system defined in claim 40, further comprising means for varying said one of said wavelengths.

* * * * *